United States Patent [19]

Pedersen et al.

[11] Patent Number: 5,817,495
[45] Date of Patent: Oct. 6, 1998

[54] $H_2O_2$-STABLE PEROXIDASE VARIANTS

[75] Inventors: Anders Hjelholt Pedersen; Jesper Vind, both of Lyngby; Allan Svendsen, Birkerød, all of Denmark; Joel R. Cherry; Michael Lamsa, both of Davis, Calif.; Palle Schneider, Ballerup; Birger Rostgaard Jensen, Væløse, both of Denmark

[73] Assignee: Novo Nordisk A/S, Bagsvaerd, Denmark

[21] Appl. No.: 624,545

[22] PCT Filed: Oct. 13, 1994

[86] PCT No.: PCT/DK94/00382

§ 371 Date: May 7, 1996

§ 102(e) Date: May 7, 1996

[87] PCT Pub. No.: WO95/10602

PCT Pub. Date: Apr. 20, 1995

[30] Foreign Application Priority Data

Oct. 13, 1993 [DK] Denmark ................. 1141/93
Aug. 29, 1994 [DK] Denmark ................. 995/94

[51] Int. Cl.[6] ............... C12N 9/08; C11D 7/54; C11D 7/42

[52] U.S. Cl. .......... 435/192; 435/172.3; 536/23.2; 252/186.1; 252/186.27; 252/186.28; 252/186.29; 252/186.3; 252/186.31; 252/186.38; 510/305; 510/374

[58] Field of Search ................... 435/192, 172.3; 536/23.2; 252/174.12, 94, 95, 99, 186.1, 186.27, 186.28, 186.29, 186.3, 186.31, 186.38; 510/305, 374

[56] References Cited

FOREIGN PATENT DOCUMENTS

| | | |
|---|---|---|
| 0 179 486 | 4/1986 | European Pat. Off. . |
| 0 299 682 | 1/1989 | European Pat. Off. . |
| WO 89/09813 | 10/1989 | WIPO ............ C11D 3/395 |
| 91/05839 | 5/1991 | WIPO . |
| 91/05858 | 5/1991 | WIPO . |
| 92/16634 | 10/1992 | WIPO . |
| 93/24618 | 12/1993 | WIPO . |

*Primary Examiner*—Rebecca E. Prouty
*Attorney, Agent, or Firm*—Steve T. Zelson, Esq.; Valeta Gregg, Esq.

[57] ABSTRACT

The present invention relates to a novel variant of peroxidase with improved stability at alkaline conditions, and a bleaching or detergent composition comprising the peroxidase variant.

13 Claims, 1 Drawing Sheet

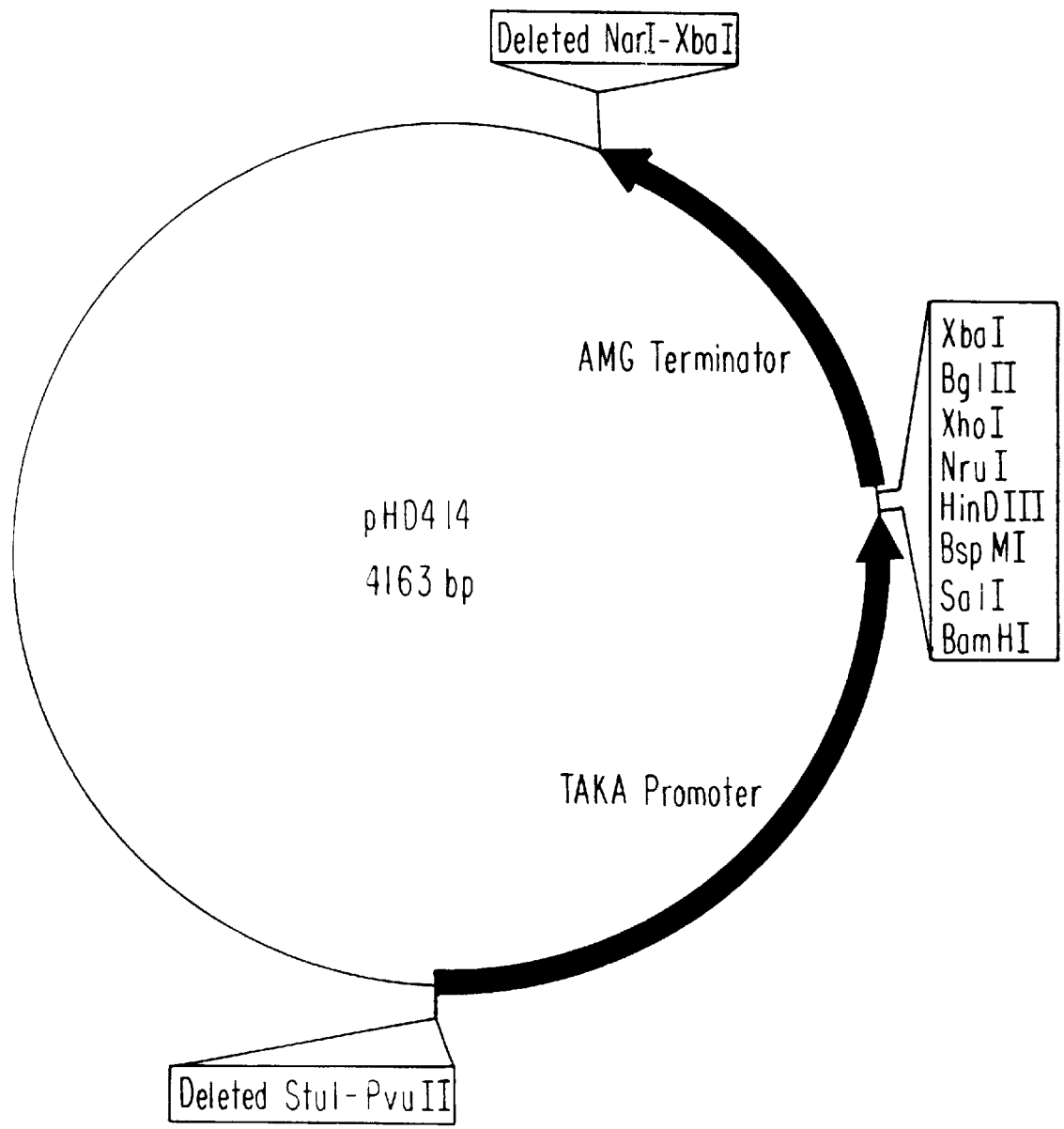

$H_2O_2$-STABLE PEROXIDASE VARIANTS

CROSS-REFERENCE TO RELATED APPLICATIONS

This application is a 371 of PCT/DK94/00382 filed Oct. 13, 1994, which is incorporated herein by reference.

FIELD OF INVENTION

The present invention relates to a novel variant of peroxidase, and a bleaching or detergent composition comprising the peroxidase variant.

BACKGROUND OF THE INVENTION

The use of bleaching agents in washing procedures and as constituents of detergent compositions is well known in the art. Thus, bleaching agents are incorporated in or sold as constituents of a major part of the commercially available detergent compositions. Important conventional bleaching agents incorporated in detergent compositions are compounds which act as precursors of hydrogen peroxide formed in the course of the washing procedure. Perborates and percarbonates are the most important examples of compounds which are employed as bleaching agents and which exert a bleaching effect in this fashion. The detailed mechanism of bleaching by means of these bleaching agents is not known at present, but it is generally assumed that the hydrogen peroxide formed during washing converts coloured substances (responsible for stains on fabric) into non-coloured materials by oxidation and that some oxidation of the coloured substances may also take place due to their direct interaction with perborate or percarbonate.

It has been found that peroxidases, utilizing hydrogen peroxide as substrate, are able to enhance the bleaching effect of hydrogen peroxide during washing. The use of peroxidases for bleaching stains on fabrics is described in WO 89/09813. It was also found that coloured substances leached from dyed fabrics could be bleached by means of peroxidases together with hydrogen peroxide. The use of peroxidases for inhibiting dye transfer in this way is described in WO 91/05839.

SUMMARY OF THE INVENTION

It has surprisingly been found that peroxidase variants with an improved stability towards hydrogen peroxide at alkaline conditions may be prepared by recombinant DNA techniques.

Accordingly, the present invention relates to a peroxidase variant with improved hydrogen peroxide stability at alkaline conditions, characterized by insertion, deletion or substitution of one or more amino acid residues in the region from amino acid residue 48 to 56, 76, 109, 214, 239, 258 to 262, 264, 266 to 272 of the parent peroxidase, a *Coprinus cinereus* peroxidase encoded by the sequence shown in SEQ ID 1.

Information about the crystal structure of the parent peroxidase was obtained by X-ray diffraction, and also by aligning the amino acid sequence of the parent peroxidase to amino acid sequences of other known peroxidases (K. G. Welinder et al., "Structure and evolution of peroxidases" in Plant Peroxidase Biochemistry and Physiology, K. G. Welinder et al. (eds.), University of Copenhagen and Geneva 1993).

In the present context the term "improved hydrogen peroxide stability" is intended to indicate that the peroxidase variant is at least 10% more stable than the parent peroxidase in the presence of hydrogen peroxide at a concentration of up to 20 mM $H_2O_2$. More specifically this is intended to mean that the peroxidase variant at one or more temperatures in the temperature interval of from 10° C. to 60° C. and at one or more $H_2O_2$ concentrations of up to 20 mM $H_2O_2$ has an at least 10% longer half-life than the wild type peroxidase (parent peroxidase). (Half-life is determined by fitting residual activities to 1st order decay). The term "alkaline conditions" is intended to indicate the pH-range from 7 to 11.

In other aspects, the present invention relates to a bleaching composition comprising a peroxidase variant according to the invention and a hydrogen peroxide source, optionally additionally comprising an oxidizable substrate; and to a detergent composition comprising a surfactant, a peroxidase variant according to the invention and a hydrogen peroxide source, optionally additionally comprising an oxidizable substrate.

BRIEF DESCRIPTION OF DRAWINGS

The present invention is further illustrated by reference to the accompanying drawing, in which FIG. 1 shows plasmid pHD414, which is a derivative of the plasmid p775 (described in EP 238023). Plasmid pHD414 is obtained according to Ex. 1.

DETAILED DISCLOSURE OF THE INVENTION

In the present description and claims, the following abbreviations are used:

| Amino Acids: |
| --- |
| A = Ala = Alanine |
| V = Val = Valine |
| L = Leu = Leucine |
| I = Ile = Isoleucine |
| P = Pro = Proline |
| F = Phe = Phenylalanine |
| W = Trp = Tryptophan |
| M = Met = Methionine |
| G = Gly = Glycine |
| S = Ser = Serine |
| T = Thr = Threonine |
| C = Cys = Cysteine |
| Y = Tyr = Tyrosine |
| N = Asn = Asparagine |
| Q = Gln = Glutamine |
| D = Asp = Aspartic Acid |
| E = Glu = Glutamic Acid |
| K = Lys = Lysine |
| R = Arg = Arginine |
| H = His = Histidine |

In describing peroxidase variants according to the invention, the following nomenclature is used for ease of reference:
Original amino acid:position:substituted amino acid(s)

According to this nomenclature, for instance the substitution of lysine by serine in position 48 is as shown:

K48S a deletion of lysine in the same position is shown as:

K48* and insertion of an additional amino acid residue such as tyrosine is shown as:

K48KY

Multiple substitutions are separated by pluses, i.e.:

E214L+E239L representing mutations in positions 214 and 239 substituting leucine for glutamic acid.

The parent peroxidase is encoded by the amino acid sequence shown in SEQ ID No. 1. Said sequence is derivable from *Coprinus cinereus*.

In one embodiment of the peroxidase variant of the invention, one or more amino acid residues are deleted, inserted or substituted in the region from amino acid residue 48 to 56, 76, 109, 214, 239, 258 to 262, 264, 266 to 272 of the parent peroxidase encoded by the amino acid sequence shown in SEQ ID No. 1.

In other embodiments of the peroxidase variant according to the invention, one or more amino acid residues may suitably be substituted as follows K48S,
V53K,A,
G72Q,
A91C,
N92K,
H109K,
Q118E,
M125A,P,W,G,S,T,C,Y,N,D,E,K,R,H,
in particular M125S,T,
S147Q,
I152C,
P155C,
M166A,P,W,G,S,T,C,Y,N,D,E,K,R,H,
in particular M166S,T,
N192K,
I195K,
V206R,
E214L,
K218R,
F229G,
A230C,
E239A,V,L,I,P,F,W,M,G,S,T,C,Y,N,Q,D,K,R,H,
in particular E239K,G,S,L,Q,M,
M242A,P,W,G,S,T,C,Y,N,D,E,K,R,H,
in particular M242S,T,
S244C,
S252P,
W258F,H,
M261A,V,L,I,P,F,W,G,S,T,C,Y,N,Q,D,E,K,R,H,
in particular M261F,V,I,L,Q,
M268A,V,L,I,P,F,W,G,S,T,C,Y,N,Q,D,E,K,R,H,
in particular M268F,V,I,L,Q,
Y272A,V,L,I,P,F,W,G,S,T,C,M,N,Q,D,E,K,R,H,
in particular Y272F,
M276A,P,W,G,S,T,C,Y,N,D,E,K,R,H,
in particular M276S,T,
K278R,
M279A,P,W,G,S,T,C,Y,N,D,E,K,R,H,
in particular M279S,T,
A304E,
V314P.

In an alternative embodiment, the peroxidase variant according to the invention may be a fragment of the peroxidase variant described above.

According to the invention, two or more amino acid residues of the peroxidase sequence may also be substituted as follows K41R+K48R,
V53K+Q118E,
V53A+E239G,
I152C+A91C,
P155C+A230C,
M166F+E239K,
G167N+V176L,
E214L+E239L,
R241E+E239K,
S244C+P155C,
E239K+M242I+Y272F,
M166F+E239K+M242I+Y272F,
M125L+M166F+E239K+M242I+Y272F.

According to the invention the substitutions, insertions or deletions disclosed in this invention may be combined with the substitutions, insertions or deletions disclosed in WO 93/24618, in which one or more amino acid residues are deleted, inserted or substituted in the region of from amino acid residue 79 to 94, 125, 153 to 157, 161 to 204, 242, 276 or 279 of the parent peroxidase shown in the present invention as SEQ ID No. 1. An example of such a combination is the variant M242I+Y272F+E239K, which has a very good hydrogen peroxide stability as demonstrated in Example 4.

The DNA sequence encoding a parent peroxidase may be isolated from any microorganism producing the peroxidase in question by various methods well known in the art. First a genomic DNA and/or cDNA library should be constructed using chromosomal DNA or messenger RNA from the organism that produces the peroxidase to be studied. Then, if the amino acid sequence of the peroxidase is known, homologous, labelled oligonucleotide probes may be synthesized and used to identify peroxidase-encoding clones from a genomic library of bacterial DNA, or from a fungal CDNA library. Alternatively, a labelled oligonucleotide probe containing sequences homologous to peroxidase from another strain of fungus could be used as a probe to identify peroxidase-encoding clones, using hybridization and washing conditions of lower stringency.

Another method for identifying peroxidase-producing clones involves inserting fragments of genomic DNA into an expression vector, such as a plasmid, transforming peroxidase-negative bacteria with the resulting genomic DNA library, and then plating the transformed bacteria onto agar containing a substrate for peroxidase. Those bacteria containing peroxidase-bearing plasmid will upon addition of hydrogen peroxide produce colonies surrounded by a halo of clear agar, due to oxidation of the substrate by secreted peroxidase.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR)

using specific primers, for instance as described in U.S. Pat. No. 4,683,202 or R. K. Saiki et al., *Science* 239, 1988, pp. 487–491.

Once a peroxidase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the peroxidase-encoding sequence, is created in a vector carrying the peroxidase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984, Biotechnology 2:646–639). U.S. Pat. No. 4,760,025, by Estell et al., issued Jul. 26, 1988, discloses the introduction of oligonucleotides encoding multiple mutations by performing minor alterations of the cassette, however, an even greater variety of mutations can be introduced at any one time by the Morinaga method, because a multitude of oligonucleotides, of various lengths, can be introduced.

Another method of introducing mutations into peroxidase-encoding sequences is described in Nelson and Long, *Analytical Biochemistry* 180, 1989, pp. 147–151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

According to the invention, a mutated peroxidase-coding sequence produced by one of the methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a signal sequence may be inserted prior to the peroxidase-coding sequence. For expression under the direction of control sequences, a target gene is operably linked to the control sequences in the proper reading frame. Promoter sequences that can be incorporated into plasmid vectors, and which can support the transcription of the mutant peroxidase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment, *B. subtilis* is transformed by an expression vector carrying the mutated DNA. If expression is to take place in a secreting microorganism such as *B. subtilis*, a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when present.

The host organism transformed with the DNA sequence encoding the peroxidase variant of the invention may also be a yeast, preferably a strain of Saccharomyces, e.g. *Saccharomyces cerevisiae* or *Schizosaccharomyces pombe*, or Pichia, e.g. *Pichia pastoris*.

In a currently preferred method of producing the peroxidase variant of the invention, a filamentous fungus is used as the host organism. The filamentous fungus host organism may conveniently be one which has previously been used as a host for producing recombinant proteins, e.g. a strain of *Aspergillus sp.*, such as *A. niger, A. nidulans* or *A. oryzae*. The use of *A. oryzae* in the production of recombinant proteins is extensively described in, e.g. EP 238 023.

For expression of peroxidase variants in Aspergillus, the DNA sequence coding for the peroxidase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a peroxidase, a cellulase or a glycolytic enzyme.

Examples of suitable promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease or *A. oryzae* triose phosphate isomerase.

In particular when the host organism is *A. oryzae*, a preferred promoter for use in the process of the present invention is the *A. oryzae* TAKA amylase promoter as it exhibits a strong transcriptional activity in *A. oryzae*. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the peroxidase variant from the host cell, the DNA sequence encoding the peroxidase variant may be preceded by a signal sequence which may be a naturally occurring signal sequence or a functional part thereof or a synthetic sequence providing secretion of the protein from the cell. In particular, the signal sequence may be derived from a gene encoding an *Aspergillus sp.* amylase or glucoamylase, a gene encoding a *Rhizomucor miehei* lipase or protease, or a gene encoding a Humicola cellulase, xylanase or lipase. The signal sequence is preferably derived from the gene encoding *A. oryzae* TAKA amylase, *A. niger* neutral α-amylase, *A. niger* acid-stable α-amylase, *Coprinus cinereus* or macrorhizus peroxidase, or *A. niger* glucoamylase.

The medium used to culture the transformed host cells may be any conventional medium suitable for growing Aspergillus cells. The transformants are usually stable and may be cultured in the absence of selection pressure. However, if the transformants are found to be unstable, a selection marker introduced into the cells may be used for selection.

The mature peroxidase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

To obtain a bleaching effect of the peroxidase variant, hydrogen peroxide or a precursor of hydrogen peroxide, preferably perborate or percarbonate, or a hydrogen peroxide generating enzyme system, e.g. an oxidase and its substrate, or a peroxycarboxylic acid or a salt thereof, should be present in the bleaching composition of the invention as substrate for the peroxidase variant.

While the mechanism of peroxidase bleaching of coloured substances present on fabrics or in the wash liquor has not yet been elucidated, it is currently believed that the enzyme acts by reducing hydrogen peroxide and oxidizing the coloured substance (electron donor substrate), thereby either generating a colourless substance or providing a substance which is not adsorbed to the fabric. This reaction is shown in Reaction Scheme 1 below

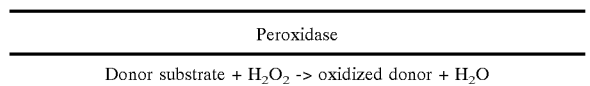

By using a peroxidase variant according to the invention which is less sensitive to hydrogen peroxide, it may be possible to add a smaller amount of the enzyme to the bleaching/washing liquor and yet obtain a satisfactory bleaching effect.

In the bleaching composition, the amount of peroxidase variant corresponds to a concentration in the wash liquor of between 0.01 and 20 PODU/ml, and the amount of hydrogen peroxide or hydrogen peroxide precursor or hydrogen peroxide generating enzyme system or percarboxylic acid or a salt thereof corresponds to a hydrogen peroxide concentration of up to 20 mM $H_2O_2$.

Determination of peroxidase activity: 1 peroxidase unit (PODU) is the amount of enzyme that catalyzes the conversion of 1 $\mu$mol hydrogen peroxide per minute at the following analytical conditions: 0.88 mM hydrogen peroxide, 1.67 mM 2,2'-azinobis (3-ethylbenzothiazoline-6-sulfonate), 0.1M phosphate buffer, pH 7.0, incubated at 30° C., photometrically followed at 418 nm.

For use of the present peroxidase variant as a bleaching composition, it has been found that the addition of another oxidizable substrate (for the peroxidase variant of the invention) at the beginning or during the washing and/or rinsing process may enhance the bleaching effect of the peroxidase variant employed. This is thought to be ascribable to the formation of radicals or other oxidized states of this substrate which participate in the bleaching or other modification of the coloured substance. Examples of such oxidizable substrates are organic compounds such as phenolic compounds, e.g. p-hydroxybenzenesulfonate. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., *Peroxidase*, London, 1964, p. 141 ff. In WO 94/12621 other types of enhancing agents are disclosed which may be used for the present purpose, e.g. phenothiazines and phenoxazines and derivatives thereof such as 10-methylphenothiazine, 10-phenothiazine-propionic acid, N-hydroxysuccinimide-10-phenothiazine-propionate, 10-ethyl-4-phenothiazine-carboxylic acid, 10-ethylphenothiazine, 10-propylphenothiazine, 10-isopropylphenothiazine, methyl-10-phenothiazinepropionate, 10-phenylphenothiazine, 10-allylphenothiazine, 10-(3-(4-methyl-1-piperazinyl)propyl)phenothiazine, 10-(2-pyrrolidinoethyl)-phenothiazine, promazine, 2-chloro-10-methylphenothiazine, 2-acetyl-10-methylphenothiazine and 10-methylphenoxazine.

The amount of oxidizable substrate corresponds to a concentration in the wash liquor of between 0.1 $\mu$M and 100 $\mu$M.

Deterrent Compositions

According to the invention, the peroxidase variant may be added as a component of a detergent composition. As such, it may be included in the detergent composition in the form of a detergent additive. The detergent composition as well as the detergent additive may additionally comprise one or more other enzymes, such as proteases, lipases, amylases, cutinases and cellulases.

In a specific aspect, the invention provides a detergent additive. The enzymes may be included in a detergent composition by adding separate additives containing one or more enzymes, or by adding a combined additive comprising all of these enzymes. A detergent additive of the invention, i.e. a separated additive or a combined additive, can be formulated e.g. as granulates, liquids, slurries, etc. Preferred detergent additive formulations are granulates, in particular non-dusting granulates, liquids, in particular stabilized liquids, slurries, or protected enzymes.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% of water and 0–30% of organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylases, lipases, cutinases, proteases and cellulases.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetri-aminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of e.g. the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O, 2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach) | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1–2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O, 2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O, 2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O, 2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O, 2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O, 2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2–3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2O$) | 5–15% |
| sodium sulfate (as $Na_2SO_4$) | 0–5% |
| zeolite (as $NaAlSiO_4$) | 15–28% |
| sodium perborate (as $NaBO_3.4H_2$) | 0–20% |
| bleach activator (TAED or NOBS) | 0–5% |
| enzymes | 0–5% |
| minor ingredients (e.g. perfume, optical brighteners) | 0–5% |

13) Detergent formulations as described in 1)–12) where the content of linear alkylbenzenesulfonate—or a part of it—is substituted by alkyl sulfate ($C_{12}$–$C_{18}$).

14) Detergent formulations a s described in 1)–13) which contain a stabilized or encapsulated peracid either as an additional component or as a substitute for already specified bleach systems.

15) Detergent compositions as described in 1), 3), 7), 9) and 12) where the content of perborate is substituted with percarbonate.

16) Detergent compositions as described in 1), 3), 7), 9) and 12) which additionally contains a Manganese catalyst. The Manganese catalyst may e.g. be one of the compounds described in "Efficient manganese catalysts for low-temperature bleaching", Nature 369, 1994, pp. 637–639.

17) Detergent composition formulated as a nonaqueous detergent liquid comprising a liquid nonionic surfactant as e.g. linear alkoxylated primary alcohol, a builder system (e.g. phosphate) enzyme and alkali. The detergent may also comprise anionic surfactant and/or a bleach system.

It is at present contemplated that, in the detergent composition of the invention, the peroxidase variant may be added in an amount corresponding to a concentration in the wash liquor of between 0.01 to 20 PODU/ml.

The present invention is further illustrated in the following examples which are not in any way intended to limit the scope of the invention as claimed.

EXAMPLE 1

Construction of a plasmid expressing the K48S variant of *Coprinus cinereus* peroxidase 1. Cloning of CDNA encoding a *Coprinus cinereus* peroxidase Construction of a Probe by PCR Peroxidase cDNA fragments were prepared by polymerase chain reaction (PCR) using specific oligonucleotide primers (R. K. Saiki et al., Science 239, 1988, pp. 487–491) constructed on the basis of the amino acid sequence of the *Coprinus macrorhizus* peroxidase. PCR was carried out using the Gene Amp kit and apparatus (available from Perkin Elmer Cetus, Norwalk, Conn., USA) in accordance with the manufacturer's instructions, with the exception that the reaction was conducted at 28° C. for the first three cycles in order to obtain better hybridisation to the first strand cDNA (prepared from mRNA obtained from *Coprinus cinereus*, IFO 8371) and subsequently at 65° C. for 30 cycles of PCR.

The following specific primers were used for PCR:

```
                       T T
1. 5'-GCGCGAATTCGTNGGNATNAACCACGG-3' (SEQ ID NO:2)

A A
2. 3'-TACAGNTTGACGGGNGGCCTAGGCG-5' (SEQ ID NO:3)

A    T T
3. 5'-GCGAATTCACNCCNCAGGTNTTCGACAC-3' (SEQ ID NO:4)

A     T A
4. 3'-GGNAAGGGNCCNCTCAAGCCTAGGCG-5' (SEQ ID NO:5)

A
5. 5'-GCGCGAATTCTGGCAGTCNAC-3' (SEQ ID NO:6)

A
6. 5'-GCGCGAATTCTGGCAGAGNATG-3' (SEQ ID NO:7)

T
7. 3'-CGNTACCGNTTCTACAGCCTAGG-5' (SEQ ID NO:8)
```

"N" denoting a mixture of all four nucleotides.

The primers were combined as follows: 1 with 2, 3 with 4, 5 with 7, 6 with 7, 1 with 4, 1 with 7 and 3 with 7. The PCR fragments were thus extended with an EcoRI site at the 5'-end and a BamHI site at the 3'-end. The PCR reactions were analyzed on a 1% agarose gel. Bands of the expected size were found in all reactions. To verify that the bands corresponded to peroxidase-specific sequences, the gel was subjected to Southern blotting and hybridised to an oligonucleotide probe with the following sequence

```
        T A A A T
5'-GTCTCGATGTAGAACTG-3' (SEQ ID NO:9)
        T
``` which is positioned between PCR primers 3 and 4. The probe was found to hybridise to bands of approximately 130 bp, 420 bp, 540 bp and 240 bp, thus confirming that the DNA bands observed correspond to peroxidase sequences.

DNA from the various PCR reactions was digested with EcoRI and BamHI and cloned into the plasmid pUC19 (C. Yanisch-Perron et al., Gene 33 1985, pp. 103–119). Colonies containing the correct PCR fragments were identified by hybridisation using the oligonucleotide probe specified above. DNA from positive colonies was analyzed by restriction enzyme mapping and partial DNA sequence analysis as described by Sanger et al., Proc. Nati. Acad. Sci. USA 74, 1977, pp. 5463–5467. A 430 bp fragment from one of the clones, obtained by using primer 1 and 4, was used to screen a *Corrinus cinereus* cDNA library as described below.

Construction of a *Coprinus cinereus* cDNA library in *E. coli*

Total RNA was extracted from homogenized *Coarinus cinereus* (IFO 8371) mycelium, collected at the time for maximum activity of the peroxidase by methods as described by Boel et al. (EMBO J. 3. 1097–1102, 1984) and Chirgwin et al. (Biochemistry (Wash), 18: 5294–5299, 1979). Poly(A)-containing RNA is obtained by two cycles of affinity chromatography on oligo(dT)-cellulose as described by Aviv and Leder (PNAS, USA 69:1408–1412, 1972). cDNA is synthesized by means of a cDNA synthesis kit from Invitrogen according to the manufacturer's instructions. About 50.000 *E. coli* recombinants from the *Cotrinus cinereus* cDNA library were transferred to Whatman 540 paper filters. The colonies were lysed and immobilized as described by Gergen et al. (Nuclei Acids Res. 7, 2115–2135, 1979). The filters were hybridized with the $^{32}$P-labelled 430 bp peroxidase-specific probe in 0.2×SSC, 0.1% SDS. Hybridization and washing of the filters were conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Bimnboim and Doly Nucleic Acids Res. 7, 1513–1523, 1979), and the DNA sequence of the cDNA insert was determined by the Sanger dideoxy procedure (Sanger et al., *Proc. Natl. Acad. Sci. USA* 74, 1977, pp. 5463–5467). The peroxidase cDNA fragment was excised from the vector by cleavage with HindIII/XhoI and was purified by agarose gel electrophoresis, electroeluted and made ready for ligation reactions. The CDNA fragment was ligated to HindIII/XhoI digested pHD414 to generate pCiP in which the CDNA is under transcriptional control of the TAKA promotor from *Aspercillus oryzae* and the AMG terminator from *Aspergillus niger*.

Construction of the Aspergillus expression vector pHD414

The vector pHD414 is a derivative of the plasmid p775 (described in EP 238 023). In contrast to p775, pHD414 has a string of unique restriction sites between the promotor and the terminator.

The plasmid was constructed by removal of an approximately 200 bp long fragment (containing undesirable restriction sites) at the 3' end of the terminator, and subsequent removal of an approximately 250 bp long fragment at the 5' end of the promotor, also containing undesirable restriction sites. The 200 bp region was removed from p775 by cleavage with NarI (positioned in the pUC vector) and XbaI (positioned just 3' to the terminator), subsequent filling in the generated ends with Klenow DNA polymerase +DNTP, purification of the vector fragment on gel and relegation of the vector fragment. The DNA was transformed into *E. coli* MC1061 as described above. 10 colonies (pHD413-1 to -10) were selected and analyzed by restriction enzyme analysis. One of the clones exhibiting the expected band pattern in the restriction enzyme analysis was used in the construction of pHD414.

pHD413 was cut with StuI (positioned in the 5' end of the promoter) and PvuII (positioned in the pUC vector) and fractionated on a gel. The vector fragment was purified, relegated and transformed into *E. coli* MC1061. 12 colonies were selected and analyzed by restriction enzyme analysis. All 12 clones exhibited the expected band pattern. The plasmid pHD414 is shown in FIG. 1.

2. 3-step PCR mutagenesis:

3-step mutagenisation involves the use of four primers:

Mutagenisation primer (=A): 5'-CCT GTT CGA TCG ATT CTT AGA-3' (SEQ ID NO:10)

PCR Helper 1 (=B): 5'-TGA TCA TAG TAC CAT CTA ATT ACA TCA AGC GGC-3' (SEQ ID NO:11)

PCR Helper 2 (=C): 5'-CTG TAA TAC GAC TCA CTA-3' (SEQ ID NO:12)

PCR Handle (=D): 5'-TGA TCA GAC TAG TAC CAT-3' (SEQ ID NO:13)

Primer A and B were diluted to 20 pmole/μl. Primer C and D were diluted to 100 pmole/μl.

All 3 steps were carried out in a 10×PCR buffer containing: 100 mM Tris-HCl, pH 8.3, 500 mM KCl, 15 mM MgCl$_2$, 0.1% gelatin, 200 μl of each of 2 mM dATP, 2 mM dCTP, 2 mM dGTP, 2 mM TTP, and 200 μl of H$_2$O.

In step 1, a reaction mixture composed of 10 μl of 10×PCR buffer, 50 μl of 2×nucleotide solution, 5 μl of primer A, 5 μl of primer B, 1 μl of pCiP (0.05 μg/μl), 30 μl of H$_2$O, 0.5 μl of Taq polymerase, and 80 μl of paraffin, was run through 1 cycle consisting of 2 minutes at 94° C., 15 cycles consisting of 1 minute at 94° C., 1 minute at 50° C. and 2 minutes at 72° C., 15 cycles consisting of 1 minute at 94° C., 1 minute at 50° C. and 3 minutes at 72° C., and 1 cycle consisting of 5 minutes at 72° C.

10 μl of the PCR product were purified on an agarose gel and redissolved in 10 μl of H2O. Then, step 2 was carried out. A reaction mixture composed of 10 μl of 10×PCR buffer, 50 μl of 2×nucleotide solution, 5 μl of the purified product of step 1, 1 μl pCiP (0.05 μg/μl), 30 μl of H$_2$O, 0.5 μl of Taq polymerase, and 80 μl of paraffin, was run through 1 cycle consisting of 5 minutes at 94° C., 2 minutes at 50° C. and 10 minutes at 72° C.

To the step 2 reaction mixture, 1 μl of primer C and 1 μl of primer D were added. The PCR reaction was carried out as described for step 1.

3. Isolation of the mutated restriction fragment:

The product from step 3 was isolated from an agarose gel and re-dissolved in 20 μl H$_2$O. Then, it was digested with the restriction enzymes XbaI and KpnI in NEBuffer 2 (New England Biolabs) supplemented with bovine serum albumin (BSA) in a total volume of 20 μl at 37° C. overnight. The 570 bp XbaI/KpnI fragment was isolated from an agarose gel.

4. Ligation to expression vector pCiP:

The expression plasmid pCiP was cleaved with XbaI and KpnI under the conditions indicated above, and the large fragment was isolated from an agarose gel. To this vector, the mutated fragment isolated above was ligated and the ligation mixture was used to transform *E.coli*. The presence and orientation of the fragment were verified by cleavage of a plasmid preparation from a transformant with restriction enzymes. Sequence analysis was carried out on the double-stranded plasmid using the di-deoxy chain termination procedure developed by Sanger. The resulting plasmid is identical to pCiP except for the altered codon.

EXAMPLE 2

Construction of plasmids expressing other variants of Coprinus peroxidase

The following mutants were constructed using the same method as described in Example 1, except that other restriction enzymes were used for digesting the PCR-product and the vector used for recloning the mutated fragment. Mutations and primers used for the modifications are listed below.

| Mutation | Primer A sequence | |
|---|---|---|
| K48S | 5'-CCT GTT CGA TCG ATT CTT AGA-3' | (SEQ ID NO:14) |
| V53K | 5'-CTT AGA ATT AAA TTC CAT GAC-3' | (SEQ ID NO:15) |
| G72Q | 5'-GAT GGA GCC ATC GGC GCC TCC TTG ACC GAA TTG ACC-3' | (SEQ ID NO:16) |
| A91C | 5'-GCC TTC CCG TGC AAT GGC GGC-3' | (SEQ ID NO:17) |
| N92K | 5'-TTC CCG GCT AAA GGA GGC CTC-3' | (SEQ ID NO:18) |
| H109K | 5'-GGT ATT AAT AAA GGT GTC TCT-3' | (SEQ ID NO:19) |
| Q118E | 5'-GAT CTC ATC GAA TTC GCC ACT-3' | (SEQ ID NO:20) |

-continued

| Mutation | Primer A sequence | |
|---|---|---|
| M12SG | 5'-GCC GTC GGC GGG TCC AAC TGC-3' | (SEQ ID NO:21) |
| M125A | 5'-GCC GTC GGC GCC TCC AAC TGC-3' | (SEQ ID NO:22) |
| S147Q | 5'-ACC GGG GAT CAA GCT TGG AGG TTG GGG TTG GGA ACT-3' | (SEQ ID NO:23) |
| I152C | 5'-CCT TCG TTG TGT CCC GGG CCC-3' | (SEQ ID NO:24) |
| P1SSC | 5'-G ATC CCC GGG TGC GGA AAC ACT-3' | (SEQ ID NO:25) |
| M166G | 5'-TTG GAT CGT GGG GGC GAT GCA-3' | (SEQ ID NO:26) |
| N192K | 5'-GAG GGT TTA AAA TCG GCC ATC-3' | (SEQ ID NO:27) |
| I195K | 5'-G AAC TCG GCC AAA TTC AGG TCT-3' | (SEQ ID NO:28) |
| V206R | 5'-CTG GGT ATC GAA GCG CTG AGG GGT CGA-3' | (SEQ ID NO:29) |
| K218R | 5'-CTG AGT GGT GCC TCG GAG CAA GGT CTC-3' | (SEQ ID NO:30) |
| E214L | 5'-TCT ACA TTT TAA CCT TGC TC-3' | (SEQ ID NO:31) |
| F229G | 5'-GAG CTC CTC GGC GCC GCC GAG AGA AGG-3' | (SEQ ID NO:32) |
| A230C | 5'-CTC GGC TTT TGC GAG GAA CTC-3' | (SEQ ID NO:33) |
| E239G | 5'-TTC CCT GGC GGC TTC CGC ATG-3' | (SEQ ID NO:34) |
| E239H | 5'-TTC CCT GGC CAC TTC CGC ATG-3' | (SEQ ID NO:35) |
| E239K | 5'-TTC CCT GGC AAA TTC CGC ATG-3' | (SEQ ID NO:36) |
| E239L | 5'-TTC CCT GGC CTA TTC CGC ATG-3' | (SEQ ID NO:37) |
| E239M | 5'-TTC CCT GGC ATG TTC CGC ATG-3' | (SEQ ID NO:38) |
| E239Q | 5'-TTC CCT GGC CAA TTC CGC ATG-3' | (SEQ ID NO:39) |
| E239S | 5'-TTC CCT GGC TCA TTC CGC ATG-3' | (SEQ ID NO:40) |
| E239T | 5'-TTC CCT GGC ACA TTC CGC ATG-3' | (SEQ ID NO:41) |
| E239W | 5'-TTC CCT GGC TGG TTC CGC ATG-3' | (SEQ ID NO:42) |
| E239R | 5'-TTC CCT GGC CGA TTC CGC ATG-3' | (SEQ ID NO:43) |
| M242G | 5'-GAA TCC CGC GGG AGG TCC GAT-3' | (SEQ ID NO:44) |
| S244C | 5'-T CGC ATG AGG TGC GAT GCT CTC-3' | (SEQ ID NO:45) |
| S252P | 5'-CG GCA GGC GGT CCG CGG GTC GCG AGC-3' | (SEQ ID NO:46) |
| W258F | 5'-GCA TGC CGA TTT CAA TCC AT-3' | (SEQ ID NO:47) |
| W258H | 5'-GCA TGC CGA CAT CAA TCC AT-3' | (SEQ ID NO:48) |
| M261F | 5'-TGG CAA TCC TTT ACT AGT AGC-3' | (SEQ ID NO:49) |
| M261G | 5'-TGG CAA TCC GGG ACC AGC AGC-3' | (SEQ ID NO:50) |
| M261Y | 5'-TGG CAA TCC TAT ACC AGC AGC-3' | (SEQ ID NO:51) |
| M261V | 5'-TGG CAA TCC GTC ACC AGC AGC-3' | (SEQ ID NO:52) |
| M268L | 5'-AAT GAA GTC CTA GGC CAG CGA-3' | (SEQ ID NO:53) |
| M268G | 5'-AAT GAA GTT GGG GGC CAG CGA-3' | (SEQ ID NO:54) |
| M268A | 5'-AAT GAA GTT GCA GGC CAG CGA-3' | (SEQ ID NO:55) |
| M268F | 5'-AAT GAA GTT TTT GGC CAG CGA-3' | (SEQ ID NO:56) |
| Y272F | 5'-GGG CCA GCG CTT TCG CGC CGC C-3' | (SEQ ID NO:57) |
| Y272G | 5'-GGC CAG CGA GGG CGC GCC GCC-3' | (SEQ ID NO:58) |
| Y272A | 5'-GGC CAG CGA GCC CGC GCC GCC-3' | (SEQ ID NO:59) |
| M276S | 5'-CGC GCC GCC TTT GCC AAG ATG-3' | (SEQ ID NO:60) |
| M276I | 5'-CGC GCC GCC ATA GCC AAG ATG-3' | (SEQ ID NO:61) |
| M276H | 5'-CGC GCC GCC CAC GCC AAG ATG-3' | (SEQ ID NO:62) |
| K278R | 5'-AG AAC AGA CAT GCG CGC CAT GGC GGC-3' | (SEQ ID NO:63) |
| M279G | 5'-ATG GCC AAG GGG TCT GTT CTC-3' | (SEQ ID NO:64) |
| M279A | 5'-ATG GCC AAG GCC TCT GTT CTC-3' | (SEQ ID NO:65) |
| A304E | 5'-AT AAC AGG CGC CTC GTT GGA CAC-3' | (SEQ ID NO:66) |
| V314P | 5'-GGC CTT ACT CCC GAT GAT ATC-3' | (SEQ ID NO:67) |
| K41R + K48R | 5'-AAT TCT AAG AAT TCG GCG AAC AGG GCT CTC ACA TCG GGA CCC TTG-3' | (SEQ ID NO:68) |
| G167N + V176L | 5'-AAG CAA GTC AAC GAG CTC ATC AGG GCT GAA GCC TGC ATC GTT CAT ACG ATC CAA-3' | (SEQ ID NO:69) |
| R241E + E239K | 5'-TTC CCT GGC AAG TTC GAA ATG AGG TCC-3' | (SEQ ID NO:70) |

It should be noted that variants in position 1–29 were digested with BamHI and XbaI in NEBuffer 3 (New England Biolabs) supplemented with BSA, resulting in a 160 bp fragment. Variants in position 30–219 were digested with XbaI/KpnI in NEBuffer 2 supplemented with BSA, resulting in a 570 bp fragment. Variants in position 220–277 were digested with KpnI/MscI in NEBuffer 2 supplemented with BSA, resulting in a 170 bp fragment. Variants in position 278–363 were digested with MscI/XhoI in NEBuffer 2 supplemented with BSA, resulting in a 420 bp fragment.

EXAMPLE 3

Expression of Coprinus peroxidase variants in *Aspergillus oryzae*

Transformation of *Aspergillus oryzae* or *Aspergillus niger* (general procedure)

100 ml of YPD medium (Sherman et al., Methods in Yeast Genetics, Cold Spring Harbor Laboratory, 1981) were inoculated with spores of *A. oryzae* or *A. niger* and incubated with shaking at 37° C. overnight. The mycelium was harvested by filtration through miracloth and washed with 200 ml of 0.6M $MgSO_4$. The mycelium was suspended in 15 ml of 1.2M $MgSO_4$. 10 mM $NaH_2PO_4$, pH=5.8. The suspension was cooled on ice, and 1 ml of buffer containing 120 mg of Novozym® 234, batch 1687 was added. After 5 minutes 1 ml of 12 mg/ml BSA (Sigma type H25) was added, and incubation with gentle agitation was continued for 1.5–2.5 hours at 37° C. until a large number of protoplasts was visible in a sample inspected under the microscope.

The suspension was filtered through miracloth, the filtrate was transferred to a sterile tube and overlayered with 5 ml of 0.6M sorbitol, 100 mM Tris-HCl, pH=7.0. Centrifugation was performed for 15 minutes at 100×g, and protoplasts were collected from the top of the $MgSO_4$ cushion. 2 volumes of STC (1.2M sorbitol, 10 mM Tris-HCl, pH=7.5. 10 mM $CaCl_2$) were added to the protoplast suspension and the mixture was centrifuged for 5 minutes at 1000×g. The protoplast pellet was resuspended in 3 ml of STC and repelleted. This procedure was repeated. Finally the protoplasts were resuspended in 0.2–1 ml of STC.

100 μl of the protoplast suspension were mixed with 5–25 μg of the appropriate DNA in 10 μl of STC. Protoplasts from the A1560 strain of *A. oryzae* (IFO 4177) were mixed with pToC186 (an *A. nidulans amdS* gene carrying plasmid). The mixture was left at room temperature for 25 minutes. 0.2 ml of 60% PEG 4000 (BDH 29576), 10 mM $CaCl_2$ and 10 mM Tris-HCl, pH=7.5, were added and carefully mixed (twice) and finally 0.85 ml of the same solution was added and carefully mixed. The mixture was left at room temperature for 25 minutes, spun at 2500×g for 15 minutes and the pellet was resuspended in 2 ml of 1.2M sorbitol. After another sedimentation, the protoplasts were spread on the appropriate plates. Protoplasts from the A1560 strain transformed with pToC186 were spread on minimal plates (Cove Biochem.Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores were picked, suspended in sterile water and spread for single colonies. This procedure was repeated and spores of a single colony after the second reisolation were stored as defined transformants.

Production of recombinant *Coprinus cinereus* peroxidase variants in an *A. oryzae* strain Plasmids containing the appropriate mutations in the peroxidase gene were transformed into *A. oryzae* A1560 by cotransformation with pToC186 containing the amdS gene from *A. nidulans* as described above with a mixture of equal amounts of pCiP and pToC186 (approximately 5 µg of each). Transformants which were able to use acetamide as their sole nitrogen source were reisolated twice. After growth on YPD medium (Sherman et al. 1981) for three days culture supernatants were analyzed by a peroxidase activity assay (PODU).

EXAMPLE 4

Hydrogen Peroxide Stability

Wild-type recombinant *Coprinus cinereus* peroxidase (rCiP) and the variants E239K, Y272F, M276S, M242I+Y272F+E239K prepared as described above, were tested for their stability in the presence of $H_2O_2$.

Samples of the variants tested were purified in the following way:

5 l of culture broth were clarified by suction-filtration through Propex cloth. 3.5 l were added 1378 g of ammonium sulphate (final concentration 2.5M) with gentle stirring. The mixture was left at 5° C. for 16 h. The precipitate was collected by centrifugation at 2500*g for 30 min at 50° C. The precipitate was redissolved in a $CaCl_2$ solution (5 mM), final volume was 200 ml. 30 ml of this solution were dialysed against a 12.5 mM Bis-tris pH 6.0 buffer; 5 l for 4 h and 5 l for 16 h. Final volume was 68 ml.

23 ml of dyalysate were applied to a Q-Sepharose HP column (Pharmacia, 26 mm Ø, 100 mm bed height). The column was equilibrated with 12.5 mM Bis-tris pH 6.0 buffer. Flow rate 4 ml/min. 400 ml of starting buffer were passed over the column, and then a linear gradient of 0.25M NaCl in 12.5 mM Bis-tris pH 6.0 buffer was applied. Total gradient volume 540 ml. 10 ml fractions were collected. The peroxidase eluted in 20 ml at 0.16M NaCl. 4 ml were applied to a column of Sephadex G 25 SF (16 mm Ø 400 mm) packed in 0.1M sodium phosphate pH 7 at a flow rate of 4 ml/min. 2 ml fractions were collected. The peroxidase was eluted in 6 ml.

Conditions for testing hydrogen peroxide stability:

| Enzyme | 25 nM |
|---|---|
| Hydrogen peroxide | 0.2 mM |
| Temperature | 30° C. |
| pH | 10.5 |
| Carbonate buffer | 20 mM |

Reagents

Sodium carbonate buffer 22 mM pH 10.5: 1.807 g of $Na_2CO_3$ and 0.416 g of $NaHCO_3$ are dissolved in deionised water to a final volume of 1 l. pH is checked.

$H_2O_2$: 2.2 mM.

Peroxidase solution: The pool from Sephadex G25 SF is diluted with sodium carbonate buffer 22 mM pH 10.5 to $OD_{404}$=0.0030. (This corresponds to 27.5 nM).

Accomplishment

The sodium carbonate buffer is preheated to 30° C. The peroxidase solution is made. A sample of the peroxidase solution is immediately withdrawn and diluted and submitted to the ABTS-assay. 5 ml of the peroxidase solution are mixed with 0.5 ml of 2.2 mM $H_2O_2$ and the mixture is placed in a water bath at 30° C. After 4, 8, 12 and 16 min samples are withdrawn, diluted and submitted to the ABTS-assay. Residual activities are fitted to 1st order decay and half-lives are calculated. rCiP is always included.

The results of the hydrogen peroxide stability test are presented in Table 1 below.

TABLE 1

| Variant | $T_{1/2}$ (min) | Index |
|---|---|---|
| rCiP | 6.5 | 1.00 |
| E239K | 8.3 | 1.27 |
| Y272F | 8.7 | 1.34 |
| M276S | 7.3 | 1.13 |
| M242I + Y272F + E239K | 14.8 | 2.27 |

We claim:

1. A peroxidase variant with improved hydrogen peroxide stability at alkaline conditions, characterized by substitution of an amino acid at one or more of positions 48, 53, 239, 258, 261, and 272 of the amino acid sequence of SEQ ID NO:1, wherein the amino acid substitution is one or more of K48S;
V53K,A;
E239A,V,L,I,P,F,W,M,G,S,T,C,Y,N,Q,D,K,R,H;
W258F,H; and
Y272A,V,L,I,P,F,W,G,S,T,C,M,N,Q,D,E,K,R,H.

2. A peroxidase variant according to claim 1, wherein the amino acid residue substituted is one or more of E239K,G,S,L,Q,M and Y272F.

3. A peroxidase variant with improved hydrogen peroxide stability at alkaline conditions, characterized by having a substitution of the amino acid sequence of SEQ ID NO:1 selected from the group consisting of:

G72Q;
A91C;
N92K;
Q118E;
S147Q;
I152C;
P155C;
N192K;
I195K;
V206R;
K218R;
F229G;
A230C;
S244C;
S252P;
K278R;
A304E;
V314P;
K41R+K48R;
V53K+Q118E;
V53A+E239G;
I152C+A91C;
P155C+A230C;
M166F+E239K;
G167N+V176L;
E214L+E239L;
R241E+E239K;
S244C+P155C;
E239K+M242I+Y272F;
M166F+E239K +M242I+Y272F; and
M125L+M166F+E239K+M242I+Y272F.

4. A peroxidase variant which is a fragment of a peroxidase variant according to claim 1.

5. A bleaching composition comprising a peroxidase variant according to claim 1 and hydrogen peroxide or a hydrogen peroxide precursor, or a hydrogen peroxide generating enzyme system, or a peroxycarboxylic acid or a salt thereof.

6. A bleaching composition according to claim 5, wherein the amount of peroxidase variant corresponds to a concentration in the wash liquor of between 0.01 and 20 PODU/ml, and the amount of hydrogen peroxide or hydrogen peroxide precursor or hydrogen peroxide generating enzyme system or peroxycarboxylic acid or a salt thereof corresponds to a hydrogen peroxide concentration in the wash liquor of up to 20 mM $H_2O_2$.

7. A bleaching composition according to claim 5, which additionally comprises an oxidizable substrate selected from the group consisting of a phenolic compound, a derivative of a phenothiazine, or a derivative of a phenoxazine.

8. A bleaching composition according to claim 7, wherein the amount of oxidizable substrate corresponds to a concentration in the wash liquor of between 0.1 $\mu$M and 100 $\mu$M.

9. A detergent composition comprising a surfactant, a peroxidase variant according to claim 1 and hydrogen peroxide or a hydrogen peroxide precursor, or a hydrogen peroxide generating enzyme system, or a peroxycarboxylic acid or a salt thereof.

10. A detergent composition according to claim 9, wherein the amount of peroxidase variant corresponds to a concentration in the wash liquor of between 0.01 to 20 PODU/ml, and the amount of hydrogen peroxide or hydrogen peroxide precursor or hydrogen peroxide generating enzyme system or peroxycarboxylic acid or a salt thereof corresponds to a hydrogen peroxide concentration in the wash liquor of up to 20 mM $H_2O_2$.

11. A detergent composition according to claim 9, which additionally comprises an oxidizable substrate selected from the group consisting of a phenolic compound, a derivative of a phenothiazine, or a derivative of a phenoxazine.

12. A detergent composition according to claim 11, wherein the amount of oxidizable substrate corresponds to a concentration in the wash liquor of between 0.1 $\mu$M and 100 $\mu$M.

13. A peroxidase variant with improved hydrogen peroxide stability at alkaline conditions, characterized by substitution of an amino acid at one or more of position 53, 239, and 272 of the amino acid sequence of SEQ ID NO:1, wherein the amino acid substitution is one or more of

V53K,A;

E239A,V,L,I,P,F,W,M,G,S,T,C,Y,N,Q,D,K,R,H; and
Y272A,V,L,I,P,F,W,G,S,T,C,M,N,Q,D,E,K,R,H.

* * * * *

SEQUENCE LISTING ( 1 ) GENERAL INFORMATION:

( i i i ) NUMBER OF SEQUENCES: 70

( 2 ) INFORMATION FOR SEQ ID NO:1:

( i ) SEQUENCE CHARACTERISTICS:
        ( A ) LENGTH: 343 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:1:

| Gln | Gly | Pro | Gly | Gly | Gly | Gly | Ser | Val | Thr | Cys | Pro | Gly | Gly | Gln | Ser |
|---|---|---|---|---|---|---|---|---|---|---|---|---|---|---|---|
| 1 | | | | 5 | | | | | 10 | | | | | 15 | |
| Thr | Ser | Asn | Ser | Gln | Cys | Cys | Val | Trp | Phe | Asp | Val | Leu | Asp | Asp | Leu |
| | | | 20 | | | | 25 | | | | | 30 | | | |
| Gln | Thr | Asn | Phe | Tyr | Gln | Gly | Ser | Lys | Cys | Glu | Ser | Pro | Val | Arg | Lys |
| | | 35 | | | | | 40 | | | | | 45 | | | |
| Ile | Leu | Arg | Ile | Val | Phe | His | Asp | Ala | Ile | Gly | Phe | Ser | Pro | Ala | Leu |
| 50 | | | | | | 55 | | | | | 60 | | | | |
| Thr | Ala | Ala | Gly | Gln | Phe | Gly | Gly | Gly | Ala | Asp | Gly | Ser | Ile | Ile |
| 65 | | | | | 70 | | | | 75 | | | | | 80 |
| Ala | His | Ser | Asn | Ile | Glu | Leu | Ala | Phe | Pro | Ala | Asn | Gly | Gly | Leu | Thr |
| | | | | 85 | | | | | 90 | | | | | 95 | |
| Asp | Thr | Val | Glu | Ala | Leu | Arg | Ala | Val | Gly | Ile | Asn | His | Gly | Val | Ser |
| | | | 100 | | | | | 105 | | | | | 110 | | |
| Phe | Gly | Asp | Leu | Ile | Gln | Phe | Ala | Thr | Ala | Val | Gly | Met | Ser | Asn | Cys |
| | | | 115 | | | | | 120 | | | | | 125 | | |
| Pro | Gly | Ser | Pro | Arg | Leu | Glu | Phe | Leu | Thr | Gly | Arg | Ser | Asn | Ser | Ser |
| | 130 | | | | | 135 | | | | | 140 | | | | |
| Gln | Pro | Ser | Pro | Pro | Ser | Leu | Ile | Pro | Gly | Pro | Gly | Asn | Thr | Val | Thr |
| 145 | | | | | 150 | | | | | 155 | | | | | 160 |
| Ala | Ile | Leu | Asp | Arg | Met | Gly | Asp | Ala | Gly | Phe | Ser | Pro | Asp | Glu | Val |
| | | | | 165 | | | | | 170 | | | | | 175 | |
| Val | Asp | Leu | Leu | Ala | Ala | His | Ser | Leu | Ala | Ser | Gln | Glu | Gly | Leu | Asn |
| | | | 180 | | | | | 185 | | | | | 190 | | |
| Ser | Ala | Ile | Phe | Arg | Ser | Pro | Leu | Asp | Ser | Thr | Pro | Gln | Val | Phe | Asp |
| | | | 195 | | | | 200 | | | | | 205 | | | |
| Thr | Gln | Phe | Tyr | Ile | Glu | Thr | Leu | Leu | Lys | Gly | Thr | Thr | Gln | Pro | Gly |
| | 210 | | | | | 215 | | | | | 220 | | | | |
| Pro | Ser | Leu | Gly | Phe | Ala | Glu | Glu | Leu | Ser | Pro | Phe | Pro | Gly | Glu | Phe |
| 225 | | | | | 230 | | | | | 235 | | | | | 240 |
| Arg | Met | Arg | Ser | Asp | Ala | Leu | Leu | Ala | Arg | Asp | Ser | Arg | Thr | Ala | Cys |
| | | | | 245 | | | | | 250 | | | | | 255 | |
| Arg | Trp | Gln | Ser | Met | Thr | Ser | Ser | Asn | Glu | Val | Met | Gly | Gln | Arg | Tyr |
| | | | 260 | | | | | 265 | | | | | 270 | | |
| Arg | Ala | Ala | Met | Ala | Lys | Met | Ser | Val | Leu | Gly | Phe | Asp | Arg | Asn | Ala |
| | | 275 | | | | | 280 | | | | | 285 | | | |
| Leu | Thr | Asp | Cys | Ser | Asp | Val | Ile | Pro | Ser | Ala | Val | Ser | Asn | Asn | Ala |
| | 290 | | | | | 295 | | | | | 300 | | | | |
| Ala | Pro | Val | Ile | Pro | Gly | Gly | Leu | Thr | Val | Asp | Asp | Ile | Glu | Val | Ser |
| 305 | | | | | 310 | | | | | 315 | | | | | 320 |
| Cys | Pro | Ser | Glu | Pro | Phe | Pro | Glu | Ile | Ala | Thr | Ala | Ser | Gly | Pro | Leu |
| | | | | 325 | | | | | 330 | | | | | 335 | |
| Pro | Ser | Leu | Ala | Pro | Ala | Pro | | | | | | | | | |
| | | | 340 | | | | | | | | | | | | |

(2) INFORMATION FOR SEQ ID NO:2:

(i) SEQUENCE CHARACTERISTICS:
(A) LENGTH: 27 base pairs
(B) TYPE: nucleic acid ( C ) STRANDEDNESS: single
( D ) TOPOLOGY: linear ( x i ) SEQUENCE DESCRIPTION: SEQ ID NO:2:

GCGCGAATTC GTNGGNATNA ANCANGG  27

( 2 ) INFORMATION FOR SEQ ID NO:3:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

GCGGATCCGG NGGNCANTTN GACAT  25

( 2 ) INFORMATION FOR SEQ ID NO:4:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( x i ) SEQUENCE DESCRIPTION: SEQ ID NO:4:

GCGAATTCAC NCCNCANGTN TTNGACAC  28

( 2 ) INFORMATION FOR SEQ ID NO:5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

GCGGATCCNA ACNCNCCNGG NAANGG  26

( 2 ) INFORMATION FOR SEQ ID NO:6:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:6:

GCGCGAATTC TGGCANTCNA C  21

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:7:

GCGCGAATTC TGGCANAGNA TG  22

( 2 ) INFORMATION FOR SEQ ID NO:8:

( i ) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GGATCCGACA TNTTNGCCAT NGC                                    23

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

GTNTNNATNT ANAANTG                                           17

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

CCTGTTCGAT CGATTCTTAG A                                      21

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:11:

TGATCATAGT ACCATCTAAT TACATCAAGC GGC                         33

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

CTGTAATACG ACTCACTA                                          18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

TGATCAGACT AGTACCAT                                          18

(2) INFORMATION FOR SEQ ID NO:14:

(i) SEQUENCE CHARACTERISTICS:

( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:14:

CCTGTTCGAT CGATTCTTAG A 21

( 2 ) INFORMATION FOR SEQ ID NO:15:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:15:

CTTAGAATTA AATTCCATGA C 21

( 2 ) INFORMATION FOR SEQ ID NO:16:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:16:

GATGGAGCCA TCGGCGCCTC CTTGACCGAA TTGACC 36

( 2 ) INFORMATION FOR SEQ ID NO:17:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:17:

GCCTTCCCGT GCAATGGCGG C 21

( 2 ) INFORMATION FOR SEQ ID NO:18:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:18:

TTCCCGGCTA AAGGAGGCCT C 21

( 2 ) INFORMATION FOR SEQ ID NO:19:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:19:

GGTATTAATA AAGGTGTCTC T 21

( 2 ) INFORMATION FOR SEQ ID NO:20:

( i ) SEQUENCE CHARACTERISTICS:
            ( A ) LENGTH: 21 base pairs
            ( B ) TYPE: nucleic acid ( C ) STRANDEDNESS: single
( D ) TOPOLOGY: linear ( x i ) SEQUENCE DESCRIPTION: SEQ ID NO:20:

GATCTCATCG AATTCGCCAC T                                    21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GCCGTCGGCG GGTCCAACTG C                                    21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

GCCGTCGGCG CCTCCAACTG C                                    21

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ACCGGGGATC AAGCTTGGAG GTTGGGGTTG GGAACT                    36

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

CCTTCGTTGT GTCCCGGGCC C                                    21

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GATCCCCGGG TGCGGAAACA CT                                   22

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

TTGGATCGTG GGGGCGATGC A    21

( 2 ) INFORMATION FOR SEQ ID NO:27:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

GAGGGTTTAA AATCGGCCAT C    21

( 2 ) INFORMATION FOR SEQ ID NO:28:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

GAACTCGGCC AAATTCAGGT CT    22

( 2 ) INFORMATION FOR SEQ ID NO:29:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

CTGGGTATCG AAGCGCTGAG GGGTCGA    27

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

CTGAGTGGTG CCTCGGAGCA AGGTCTC    27

( 2 ) INFORMATION FOR SEQ ID NO:31:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TCTACATTTT AACCTTGCTC    20

( 2 ) INFORMATION FOR SEQ ID NO:32:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

GAGCTCCTCG GCGCCGCCGA GAGAAGG 27

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:33:

CTCGGCTTTT GCGAGGAACT C 21

(2) INFORMATION FOR SEQ ID NO:34:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:34:

TTCCCTGGCG GCTTCCGCAT G 21

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:35:

TTCCCTGGCC ACTTCCGCAT G 21

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:36:

TTCCCTGGCA AATTCCGCAT G 21

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:37:

TTCCCTGGCC TATTCCGCAT G 21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:38:

TTCCCTGGCA TGTTCCGCAT G 21

( 2 ) INFORMATION FOR SEQ ID NO:39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

TTCCCTGGCC AATTCCGCAT G    21

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

TTCCCTGGCT CATTCCGCAT G    21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TTCCCTGGCA CATTCCGCAT G    21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

TTCCCTGGCT GGTTCCGCAT G    21

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

TTCCCTGGCC GATTCCGCAT G    21

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

GAATCCCGCG GGAGGTCCGA T    21

( 2 ) INFORMATION FOR SEQ ID NO:45:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

TCGCATGAGG TGCGATGCTC TC        22

( 2 ) INFORMATION FOR SEQ ID NO:46:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

CGGCAGGCGG TCCGCGGGTC GCGAGC        26

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

GCATGCCGAT TTCAATCCAT        20

( 2 ) INFORMATION FOR SEQ ID NO:48:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GCATGCCGAC ATCAATCCAT        20

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

TGGCAATCCT TTACTAGTAG C        21

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

TGGCAATCCG GGACCAGCAG C        21

( 2 ) INFORMATION FOR SEQ ID NO:51:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:51:

TGGCAATCCT ATACCAGCAG C 21

( 2 ) INFORMATION FOR SEQ ID NO:52:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:52:

TGGCAATCCG TCACCAGCAG C 21

( 2 ) INFORMATION FOR SEQ ID NO:53:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:53:

AATGAAGTCC TAGGCCAGCG A 21

( 2 ) INFORMATION FOR SEQ ID NO:54:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:54:

AATGAAGTTG GGGGCCAGCG A 21

( 2 ) INFORMATION FOR SEQ ID NO:55:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:55:

AATGAAGTTG CAGGCCAGCG A 21

( 2 ) INFORMATION FOR SEQ ID NO:56:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:56:

AATGAAGTTT TTGGCCAGCG A 21

( 2 ) INFORMATION FOR SEQ ID NO:57:

( i ) SEQUENCE CHARACTERISTICS:
   ( A ) LENGTH: 22 base pairs (B) TYPE: nucleic acid
(C) STRANDEDNESS: single
(D) TOPOLOGY: linear (xi) SEQUENCE DESCRIPTION: SEQ ID NO:57:

GGGCCAGCGC TTTCGCGCCG CC 22

(2) INFORMATION FOR SEQ ID NO:58:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:58:

GGCCAGCGAG GGCGCGCCGC C 21

(2) INFORMATION FOR SEQ ID NO:59:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:59:

GGCCAGCGAG CCCGCGCCGC C 21

(2) INFORMATION FOR SEQ ID NO:60:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:60:

CGCGCCGCCT TTGCCAAGAT G 21

(2) INFORMATION FOR SEQ ID NO:61:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:61:

CGCGCCGCCA TAGCCAAGAT G 21

(2) INFORMATION FOR SEQ ID NO:62:

(i) SEQUENCE CHARACTERISTICS:
(A) LENGTH: 21 base pairs
(B) TYPE: nucleic acid
(C) STRANDEDNESS: single
(D) TOPOLOGY: linear (xi) SEQUENCE DESCRIPTION: SEQ ID NO:62:

CGCGCCGCCC ACGCCAAGAT G 21

(2) INFORMATION FOR SEQ ID NO:63:

(i) SEQUENCE CHARACTERISTICS:
(A) LENGTH: 26 base pairs
(B) TYPE: nucleic acid
(C) STRANDEDNESS: single ( D ) TOPOLOGY: linear ( x i ) SEQUENCE DESCRIPTION: SEQ ID NO:63:

AGAACAGACA TGCGCGCCAT GGCGGC 26

( 2 ) INFORMATION FOR SEQ ID NO:64:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:64:

ATGGCCAAGG GGTCTGTTCT C 21

( 2 ) INFORMATION FOR SEQ ID NO:65:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:65:

ATGGCCAAGG CCTCTGTTCT C 21

( 2 ) INFORMATION FOR SEQ ID NO:66:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:66:

ATAACAGGCG CCTCGTTGGA CAC 23

( 2 ) INFORMATION FOR SEQ ID NO:67:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:67:

GGCCTTACTC CCGATGATAT C 21

( 2 ) INFORMATION FOR SEQ ID NO:68:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:68:

AATTCTAAGA ATTCGGCGAA CAGGGCTCTC ACATCGGGAC CCTTG 45

( 2 ) INFORMATION FOR SEQ ID NO:69:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear -continued (xi) SEQUENCE DESCRIPTION: SEQ ID NO:69:

AAGCAAGTCA ACGAGCTCAT CAGGGCTGAA GCCTGCATCG TTCATACGAT CCAA 54

(2) INFORMATION FOR SEQ ID NO:70:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO:70:

TTCCCTGGCA AGTTCGAAAT GAGGTCC 27